United States Patent [19]

Anhäuser et al.

[11] Patent Number: 5,044,372

[45] Date of Patent: Sep. 3, 1991

[54] EPICUTANEOUS TEST PLASTER

[75] Inventors: Dieter Anhäuser, Melsbach; Kurt Seeger, Neuwied, both of Fed. Rep. of Germany

[73] Assignee: Lohmann GmbH & Co. KG, Neuwied, Fed. Rep. of Germany

[21] Appl. No.: 328,089

[22] Filed: Mar. 23, 1989

[30] Foreign Application Priority Data

Mar. 29, 1988 [DE] Fed. Rep. of Germany ....... 3810658

[51] Int. Cl.$^5$ ............................................. A61B 5/00
[52] U.S. Cl. .................................... 128/743; 604/307
[58] Field of Search ..................... 128/155, 156, 743; 604/304, 307

[56] References Cited

U.S. PATENT DOCUMENTS

| | | | |
|---|---|---|---|
| 2,841,138 | 7/1958 | Laub | 128/743 |
| 3,703,890 | 11/1972 | Saunders, Jr. | 604/307 |
| 3,870,593 | 3/1975 | Elton et al. | |
| 4,265,234 | 5/1981 | Schaar | 128/156 |
| 4,600,001 | 7/1986 | Gilman | 128/156 |
| 4,614,183 | 9/1986 | McCracken | 128/155 |
| 4,619,253 | 10/1986 | Anhauser et al. | 128/156 |
| 4,887,611 | 12/1989 | Rudiger et al. | 604/307 |
| 4,915,102 | 4/1990 | Kwiatek et al. | 128/156 |

Primary Examiner—Randall L. Green
Assistant Examiner—Paul Prebilic
Attorney, Agent, or Firm—Kalish & Gilster

[57] ABSTRACT

The invention relates to plasters, particularly epicutaneous test plasters with at least one active substance absorbing or receiving device (14) arranged on a carrier film (32). The carrier film (12) is made from a highly elastic polymer material, which is impermeable for liquid water, but permeable for water vapour. On the surface remote from the skin, it is detachably connected in whole-area or partial area manner with a support film (11) at least covering the surface of the carrier film. The invention also relates to processes for the production thereof and the use thereof.

8 Claims, 2 Drawing Sheets

EPICUTANEOUS TEST PLASTER

BACKGROUND AND SUMMARY OF THE INVENTION

The invention relates to plasters, particularly epicutaneous test plasters with at least one active substance receiving or absorbing device located on a carrier film as well as to a process for the production thereof and to the use thereof.

Epicutaneous plasters are used in epicutaneous tests, which are used in particular for clarifying the causes of allergic contact dermatitis. For this purpose the test substance to be tested is applied to a test plaster, which is then applied to appropriate points of the patient's skin. The test plaster is then removed after a predetermined time.

The first reading or observation of the patient's reaction to the active substance exposure takes place immediately following test plaster removal and then further readings or observations occur at given intervals of time. It is helpful to be able to mark the test points on the skin, so that it is possible to reliably find again the skin point contacted with the test substance.

In principle, epicutaneous test plasters have the following structure. On a contact adhesive carrier layer are arranged active substance-absorbing devices in the form of absorptive textiles, e.g. of woven or non-woven fabric, or containers open towards the skin, or are formed in said carrier layer being able to absorb or take up the test substances. The test plaster surface to be contacted with the skin is covered with a removable protective layer prior to application. Hitherto flat textile materials, such as e.g. woven and non-woven fabrics, polymer or metal films and foils have been proposed as the carrier layer. The disadvantage of these materials is that the carrier materials have an inadequate elasticity to completely prevent the premature detachment of the test plaster from the skin through unavoidable body movements and avoid the irritations caused by rubbing on the active substance absorbing devices, which can simulate an allergic reaction.

It is also desired, particularly in the case of Plasters which remain a long time on the skin, that they are on the one hand watertight, so that they are not damaged when the patient is washing or taking a shower, while on the other hand a permeability for water vapor is desired, in order to prevent maceration of the underlying skin layer. It has not been possible to realize this up to now.

The problem of the present invention is therefore to provide a plaster, particularly an epicutaneous plaster, which avoids the aforementioned deficiencies of the known solution proposals.

Surprisingly the problem has been solved in that the carrier film is made from a highly elastic polymer material, which is tight for liquid water, but permeable for water vapor and is detachably connected in whole-area manner or in partial surface portions on the surface remote from the skin to at least one support or backing film covering the surface of the carrier film.

In order to fulfil the requirements regarding a carrier material of an epicutaneous test plaster with respect to elasticity, watertightness and water vapor permeability, one possibility is to reduce the thickness of the polymer film, but the use of extremely thin films with these desired characteristics for such plaster types has failed up to now due to the difficulty of handling said films. They have a very limited flexural rigidity, being so-to-speak flabby, crease very easily and therefore tend to adhere to themselves on application. In order to permit the use of such films for plasters, particularly epicutaneous test plasters, the invention makes use of a surface stabilization, in which the extremely thin film is reinforced by joining to a thicker, more rigid, second film until application has taken place. This surface-stabilizing film is referred to as the support film and has at least the size of the film to be stabilized. Advantageously it is allowed to project over the film to be stabilized on at least one side, so as to provide a gripping or handling edge for the subsequent removal of the support film.

According to another preferred realization of the invention the support film projects so far over the edge of the carrier film that, parallel to said edge, is offered space for a contact adhesive marking strip separated from the carrier film and which on application of the active substance absorbing device it adheres alongside the same to the skin and, following the removal of the plaster, preferably remains on the skin and is available for marking the test point.

Said marking strip can e.g. be colored. The epicutaneous test plasters according to the invention can be in the form of individual plasters, i.e. with only a single active substance absorbing device, but preferably have several active substance absorbing devices arranged in accordance with a predetermined geometrical pattern and preferably in rows. Between the individual active substance absorbing devices can be provided predetermined breaking lines, which permit an easy separation of a plaster with the desired number of active substance absorbing devices from a longer plaster web.

The carrier film which is impermeable to liquid water and permeable to water vapor to be used according to the invention has a suitable polymer, examples of which are polyurethanes, polyvinylchlorides, polyvinylidene chlorides, polyvinyl alcohols, polypropylene, polyamides, ethylene-vinylacetate copolymers, polyesters, polycarbonates, polyvinylfluoride and other fluorine-containing polymers. Polyurethane-based carrier films are particularly preferred. The layer thicknesses of suitable carrier films are in the range 5 to 120 pm, preferably 10 to 50 $\mu$m. Their water vapor permeability should be at least 300 g/m$^2$/24 hours.

The one or multi-layer support film preferably contains suitable polymers, or also metals. Suitable polymers are e.g. polyethylene, polypropylene, polyamides and polyesters. Optionally said films are siliconized on the skin side, in order to obtain the necessary separating force between the carrier film and the support film. The film thickness can be 20 to 200 pm, preferably 30 to 80 pm. The gripping edge optionally formed on the support film must be sufficiently wide to ensure easy handling. Preferably the support film is not detachably connected to the carrier film by adhesion and instead the connection is brought about by mechanical coherence, which is e.g. obtained if the carrier film is produced directly on the support film by extrusion, molding or some other film production procedure. In the case of coextrusion of both films it must be conversely ensured that the two films can be separated from one another. The skin side of the carrier film is covered with a contact adhesive layer for which purpose the known physiologically unobjectionable contact adhesive materials are suitable. Examples are rubber, rubber-like synthetic homopolymers, copolymers and block polymers, polyacrylates and their copolymers, polyurethanes and silicones. The surface application of the contact adhesive is between 15 and 80 g/m², preferably between 30 and 50 g/m².

The active substance absorbing devices are preferably portions, such as circular disks or other surface shapes of absorptive material, such as e.g. paper, woven and non-woven fabrics and gel-like polymers, which can supply the active substance to the skin or comprise a small shell or dish for receiving the active substance, such as a test substance. They are fixed in per se known manner to the contact adhesive layer. In order to prevent an unintentional migration of the liquid active substance or active substance formulation from the active substance absorbing or receiving devices, the latter can be covered with a film ring dimensioned in such a way that with half its width it covers the active substance absorbing device and with the other half is fixed to the contact adhesive layer, without impairing the skin contact surface of the active substance absorbing device.

The plaster is preferably covered on the contact adhesive side by a protective layer prior to application. This protective layer can be in one or more parts and adjacent parts can overlap in order to form a gripping aid for removing the protective layer. In principle, all materials suitable for the support film can be used for the optionally multicoat protective layer. However, it is also possible to use in exemplified manner polytetrafluoroethylene, cellophane, polyvinylchloride, treated papers, metal foils and polymer-coated metal foils. The substance weight is 50 to 200 g/m², preferably 80 to 150 g/m2. The protective layer side in contact with the contact adhesive layer must permit a removal of the protective layer from the remainder of the plaster with a force smaller than that required for removing the support film from the carrier film.

BRIEF DESCRIPTION OF THE DRAWINGS

The invention is described in greater detail hereinafter with respect to the drawings, which are not true to scale and wherein show.

DESCRIPTION OF THE PREFERRED EMBODIMENTS

Figure 1:
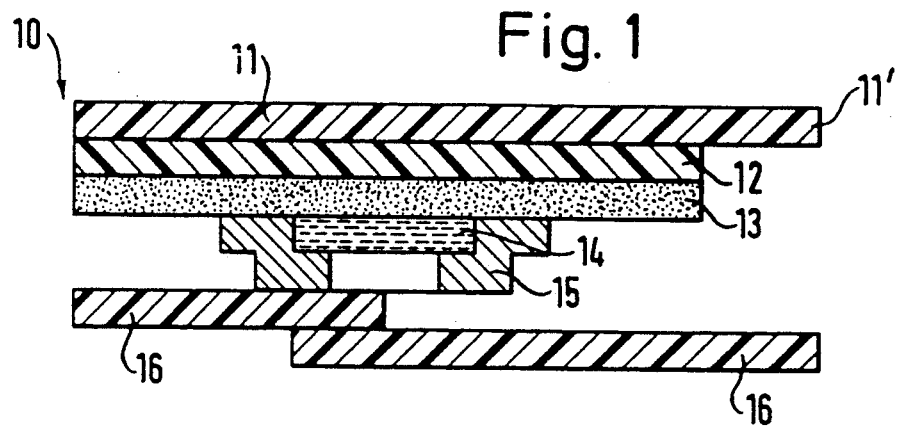
FIG. 1 diagrammatically a cross-section through a preferred embodiment of the invention.
Figure 2:
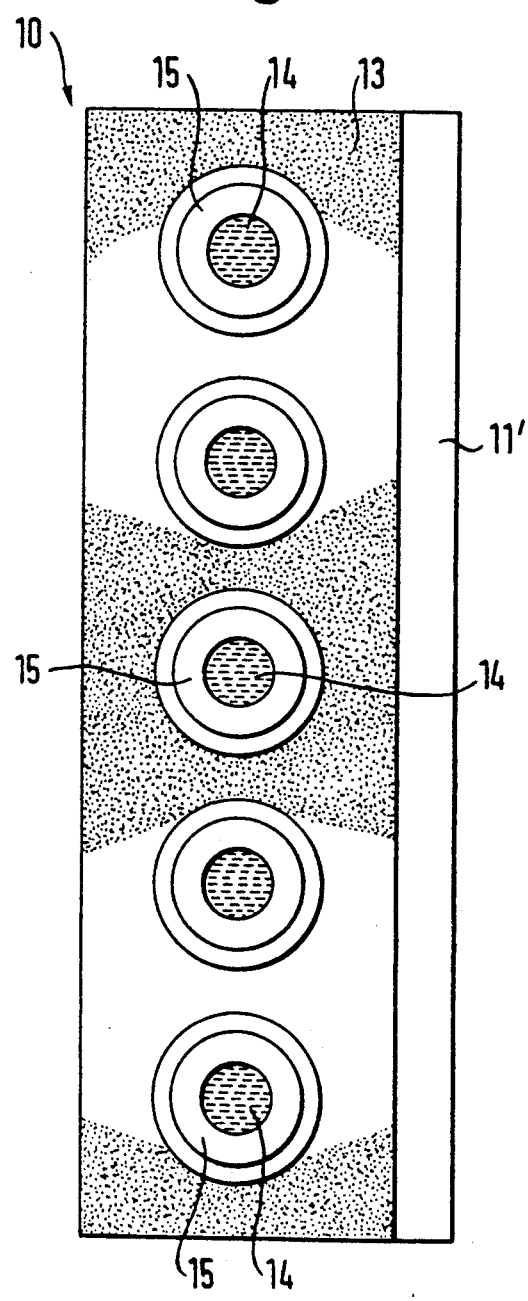
FIG. 2 diagrammatically a plan view from below of the plaster according to FIG. 1 without the protective layer.

The cross-section of a preferred embodiment of an inventive epicutaneous test plaster 10 diagrammatically shown in FIG. 1 reveals a support film 11, which projects over one edge of the carrier film 12 and therefore forms a gripping or handling portion at the time of application. The contact adhesive layer 13 has the same dimensions as the carrier film 12. The active substance absorbing or receiving device 14 and the locking ring 15 are fixed to the contact adhesive layer. A two-part protective layer 16 covers the entire plaster up to the time of application. A removal aid is formed through the overlapping of the two parts of the protective layer.

The gripping portion 11' of support film 11 can be seen in the plan view of the skin side of an inventive plaster 10 with the protective layer removed. The plaster 10 has in this case five active substance absorbing devices 14, which are arranged in rows and which are fixed together with the locking ring 15 to the contact adhesive layer 13.

Figure 3:
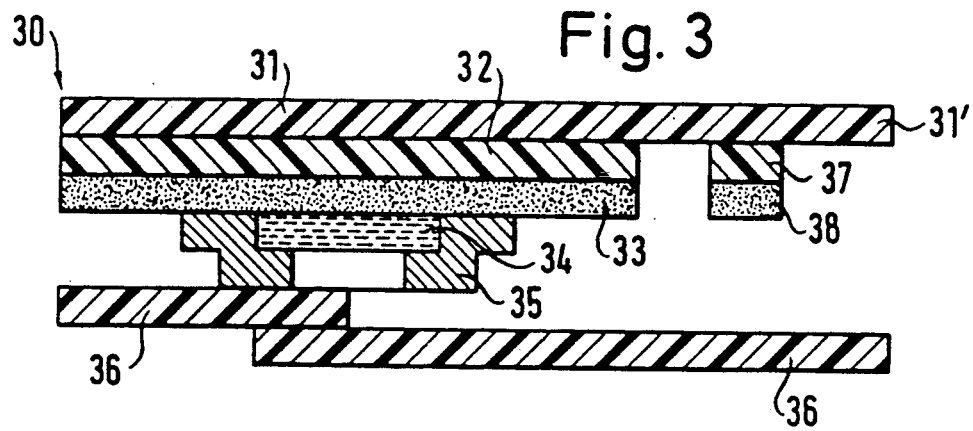
FIG. 3 diagrammatically a cross-section through a further preferred plaster construction according to the invention.

FIG. 3 diagrammatically shows a cross-section through another preferred embodiment according to the invention. A marking strip 37 is provided in the projecting edge 31' of support film 31 and, like the latter is covered with an adhesive layer 33. The further construction with the active substance absorbing device 34, locking ring 35 and protective layer 36 is in accordance with FIG. 1.

Figure 4:
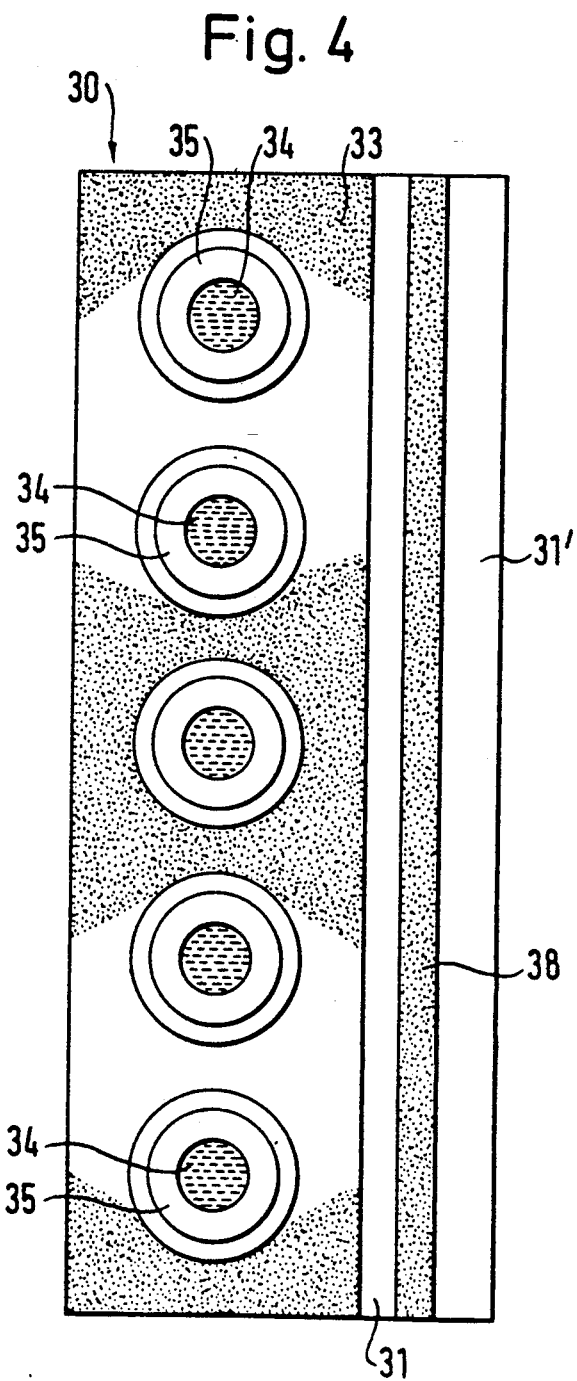
FIG. 4 diagrammatically a plan view from below of a plaster according to FIG. 3 without the protective layer.

FIG. 4 is a plan view of the skin side of the epicutaneous test plaster of FIG. 3 without the protective layer. It is possible to see the projecting edge 31' of support film 31, the skin side 38 of the adhesive layer visible through the gap between the contact adhesive carrier film 32 and the marking strip 37, the active substance absorbing device 34 and the locking ring 35.

The production of the novel means, particularly suitable as epicutaneous test plasters can, according to the invention, take place through producing a web-like carrier film by applying a polymer solution directly to a web-like support film and evaporating the solvent or solvents. Another preferred method is the formation of a laminate of support film and carrier film by coextrusion. The process parameters must be adjusted in such a way that the subsequently necessary separability of the two films is ensured. To the skin side of the thus obtained laminate is applied a contact adhesive layer by a known process, e.g. a transfer process and to which are fixed disk-like active substance absorbing devices in two rows having the desired spacing and which are parallel to the edge. Said devices are then centrally provided with film material locking rings and the edges of the rings projecting over the devices are fixed to the contact adhesive layer. Parallel to the outer edges of the web are then removed by a depth-controlled punching or cutting operation, in each case one strip from the carrier film with contact adhesive, so that an adhesive-free gripping edge is provided on the support film. For the protection of the plaster, a three-part protective layer passes over the width of the web. Either the middle part overlaps the two outer parts, or the outer parts overlap the middle part, in order to facilitate detachment again prior to use. For assembly purposes, the thus obtained laminate web is cut centrally, accompanied by the formation of two epicutaneous test plaster strips, which are cut to length in accordance with the desired number of active substance absorbing devices. However, they can also be wound onto a roll, or placed in Leporello fold form.

Prior to the separation of the wide fabric, if desired, a predetermined breaking line can be provided at certain intervals at right angles to the web direction and this permits manual removal of the appropriate length without additional tools.

For the production of another preferred embodiment of the epicutaneous test plaster, during depth-controlled punching or cutting in the aforementioned process, a marking strip of carrier film material and contact adhesive is formed, which is separate from the carrier film and is still adhering to the support film.

The following example illustrates the production process, but the invention is in no way limited thereto.

EXAMPLE

A 70 μm thick, web-like polypropylene film (1050 mm wide) siliconized on one side is so coated by means of a roll application mechanism with a mixture of 100 parts by weight of a 30% by weight solution of a polyester urethane adduct based on toluylene diisocyanate in ethyl acetate (Bayer, lmpranil C), 7.5 parts by weight of a 75% by weight solution of a crosslinking agent based on polyols and aromatic diisocyanate in ethyl acetate (Bayer, Imprafix TH), 5 parts by weight of a 10% by weight solution of an accelerator of an organic nitrogen derivative and an organometallic compound in a 1:4:4 mixture of ethyl acetate, methyl ethyl ketone/toluene (Bayer, Imprafix BE) and 75.7 parts by weight of ethyl acetate, that after evaporating the solvent at 30 to 70° C., a 42 μm thick polyurethane film is obtained.

On a silicone paper by means of roll application from a mixture of 100 parts by weight of an acrylate solution (Durotak 280 - 2516 of National Starch & Chemical BV) and 3 parts by weight of Hercolyn (Hercules) and subsequent evaporation of the solvent at 50° to 90° C., a 40 μm thick contact adhesive layer is produced and coated round the support film/carrier film laminate. The thus obtained wide fabric is cut to a width of 92 mm.

Disk-like active substance absorbing devices with a diameter of 15 mm and punched from binder-free non-woven fabric (40% staple fibre/60% cotton, 80 g/m$^2$) with a one-sided polyethylene coating are pressed in parallel rows (spacing 40 mm), with a spacing of 27.5 mm by the polyethylene side onto the contact adhesive layer. In the next stage the active substance absorbing devices are provided with polyester film locking rings (internal diameter 10 mm, external diameter 21 mm), a 6 mm wide margin or border being fixed to the adhesive layer.

The gripping edge is then produced on the support film in that in a distance of 10 mm parallel to the edges of the web, the carrier film with the contact adhesive layer is separated by a depth-controlled cutting process and the resulting strips drawn off. The web is then centrally cut open, so that two epicutaneous test plaster strips are formed, which are wound onto a roll.

Thus it is seen that the invention comprehends an epicutaneous test plaster comprising at least one active characterized in that the carrier film (12,32) is made from a highly elastic polymer material which is impermeable for liquid water but permeable for water vapor, the carrier film having a skin side carrying said active substance absorbing device and a skin-remote surface which is detachably connected over at least a partial area thereof to a support film (11,31) for at least covering the surface of the carrier film.

We claim:

1. An epicutaneous test plaster comprising one active substance absorbing device arranged on a carrier film, characterized in that the carrier film (12,32) is made from a highly elastic polymer material which is impermeable for liquid water but permeable for water vapor, the carrier film having a skin side carrying said active substance absorbing device and a skin-remote surface which is detachably connected over at least a partial area thereof a support film (11,31) for at least covering the surface of the carrier film.

2. An epicutaneous test plaster according to claim 1, wherein the support film (11,31) projects over the carrier film (12,32) along at least one edge.

3. An epicutaneous test plaster according to claims 1 or 2, further comprising a skin-side contact adhesive marking strip (37) lying parallel to at least one edge of the plaster (10,30), the contact adhesive marking strip (37) being detachably fixed to the skin-remote surface on the support film (11',31') projecting over the carrier film.

4. An epicutaneous test plaster according to claim 3, characterized in that there are a plurality of such active substance absorbing devices (14,34) arranged in rows.

5. An epicutaneous test plaster according to claim 4, characterized in that predetermined breaking lines are provided between said active substance absorbing devices (14,34).

6. An epicutaneous test plaster according to claim 5, characterized in that the material forming the carrier film (12,32) is a polyurethane-based polymer.

7. An epicutaneous test plaster according to claim 4, characterized in that said carrier film is coated with a contact adhesive layer and said active substance absorbing devices are fixed with a respective locking ring to said contact adhesive layer.

8. An epicutaneous test plaster according to claim 7 wherein said carrier film has a water vapor permeability of at least 300 g/m$^2$/24 hours.

* * * * *

UNITED STATES PATENT AND TRADEMARK OFFICE
CERTIFICATE OF CORRECTION

PATENT NO. : 5,044,372

DATED : September 3, 1991

INVENTOR(S) : D. Anhauser et al

It is certified that error appears in the above-identified patent and that said Letters Patent is hereby corrected as shown below:

Col. 6, line 17 - After "thereof" insert --to--.

Signed and Sealed this

Twentieth Day of October, 1992

*Attest:*

DOUGLAS B. COMER

*Attesting Officer*      *Acting Commissioner of Patents and Trademarks*